(12) United States Patent
Behnam

(10) Patent No.: US 9,107,446 B2
(45) Date of Patent: Aug. 18, 2015

(54) SOLUBILIZATES OF PRESERVATIVES AND METHOD FOR PRODUCING THE SAME

(75) Inventor: Dariush Behnam, Rossdorf (DE)

(73) Assignee: AQUANOVA AG, Darmstadt (DE)

( * ) Notice: Subject to any disclaimer, the term of this patent is extended or adjusted under 35 U.S.C. 154(b) by 1365 days.

(21) Appl. No.: 12/224,833

(22) PCT Filed: Jan. 8, 2007

(86) PCT No.: PCT/EP2007/000094
§ 371 (c)(1),
(2), (4) Date: Feb. 17, 2009

(87) PCT Pub. No.: WO2007/101495
PCT Pub. Date: Sep. 13, 2007

(65) Prior Publication Data
US 2009/0306210 A1 Dec. 10, 2009

(30) Foreign Application Priority Data
Mar. 7, 2006 (DE) .................. 10 2006 010 809
Nov. 3, 2006 (EP) .................. PCT/EP2006/010568

(51) Int. Cl.
| | |
|---|---|
| *A01N 37/10* | (2006.01) |
| *A01N 37/06* | (2006.01) |
| *A61K 31/192* | (2006.01) |
| *A23L 2/44* | (2006.01) |
| *A23B 7/154* | (2006.01) |
| *A23C 3/08* | (2006.01) |
| *A23C 19/10* | (2006.01) |
| *A23L 3/3463* | (2006.01) |
| *A23L 3/3508* | (2006.01) |

(52) U.S. Cl.
CPC . *A23L 2/44* (2013.01); *A01N 37/10* (2013.01); *A23B 7/154* (2013.01); *A23C 3/08* (2013.01); *A23C 19/10* (2013.01); *A23L 3/3463* (2013.01); *A23L 3/3508* (2013.01); *A61K 31/192* (2013.01); *A23V 2002/00* (2013.01)

(58) Field of Classification Search
CPC .......................... A61K 31/192; A61K 9/1075
USPC ........................................................ 514/568
See application file for complete search history.

(56) References Cited

U.S. PATENT DOCUMENTS

| | | | |
|---|---|---|---|
| 5,419,908 A * | 5/1995 | Richter et al. ............. 424/405 |
| 5,641,532 A * | 6/1997 | Pflaumer et al. ........... 426/590 |
| 6,514,943 B2 * | 2/2003 | Kovesdi et al. ............ 514/23 |
| 7,128,922 B1 * | 10/2006 | Charman et al. ........... 424/400 |
| 8,022,033 B2 * | 9/2011 | Larew et al. .............. 514/1.1 |
| 2003/0105157 A1 * | 6/2003 | Behnam .................... 514/458 |
| 2004/0081670 A1 * | 4/2004 | Behnam .................... 424/400 |
| 2007/0065470 A1 * | 3/2007 | Behnam .................... 424/401 |

FOREIGN PATENT DOCUMENTS

| | | |
|---|---|---|
| DE | 2519557 | 11/1976 |
| DE | 2623682 | 12/1976 |
| DE | 60103023 T2 | 1/2005 |
| EP | 0572190 A1 | 12/1993 |
| EP | 0659347 A1 | 6/1995 |
| EP | 1475083 A1 | 2/2002 |
| EP | 1259113 | 4/2004 |
| JP | 2003-238957 | 8/2003 |
| WO | WO 2005/046349 * | 5/2005 |

OTHER PUBLICATIONS

Cole et al. (Yeast, 2:93-100, 1986).*
Anthanasios M. Gerakis et al., Micellar acid-base potentiometric titrations of weak acidic and/or insoluble drugs, Journal of Pharmaceutical & Biomedical Analysis, 1993, pp. 33-41, vol. 11, No. 1, Pergamon Press Ltd., Great Britain.

* cited by examiner

*Primary Examiner* — Bong-Sook Baek
(74) *Attorney, Agent, or Firm* — Jacobson Holman PLLC

(57) ABSTRACT

Described is a solubilizate of a preservative containing an aliphatic and/or aromatic acid such as sorbic acid and/or benzoic acid that is free of stabilizing agents, as well as one or more emulsifiers with an HLB value between 9 and 18 with a concentration of about 50% and about 95% emulsifier with regard to the total quantity of the solubilizate, and a procedure for the production of such a solubilizate.

13 Claims, 2 Drawing Sheets

SOLUBILIZATES OF PRESERVATIVES AND METHOD FOR PRODUCING THE SAME

This is a national stage of PCT/EP07/000094 filed Jan. 8, 2007 and published in German.

The invention concerns the solubilisate of a preserving agent.

In the German Patent Application Publication 26 23 682, a procedure for manufacturing a suspension and an emulsion from sorbic acid is described, in which a heated solution of sorbic acid is atomized in a solvent made from water, displaced with a water-soluble, organic solvent with a low boiling point; the resulting fluid is then cooled quickly and the excess solvent is removed. Because of the warming and atomization of the sorbic acid solution, this procedure is very complex.

In the document DE 25 19 557, a disinfecting soap is described, which, besides the disinfectant and the non-ionic emulsifier, such as a polysorbate for example, contains a considerable amount of diluent as well as other additional substances as galenicals. This soap disinfects hands or other skin areas in the medical field.

The text DE 601 03 023 T2 discloses acidic anti-microbial mixtures for the treatment of foodstuffs, which includes an organic acid, a likewise non-ionic surfactant and a stabilizing agent, for example a polysorbate. With considerable dilution, the mixture can be used for treating the surfaces of foodstuffs in order to reduce microbial growth.

For the preservation of foodstuffs against microbial rotting, there is, in addition to the biological and chemical acidification as well as the heating process, the chemical preservation with bactericidal or bacteriostatic chemicals.

The most common preservatives for beverages are sorbic acid (E200 and salts E201-3) and benzoic acid (E201 and salt 211-13).

Benzoic acid (BS) works mainly against yeast and molds; bacteria are only partially stopped. Sorbic acid (SS) works likewise against yeasts and molds, but somewhat better against bacteria, primarily against catalase-positive and anaerobic bacteria. In practice, a mixed preservative of equal parts benzoic acid and sorbic acid proved to have a certain synergistic effect. It is also possible to reduce in this way the adverse effect on the taste of the foodstuff caused by high amounts of preservatives. Usual amounts are 150-200 ppm per preservative in the finished product. The maximum amounts for non-alcoholic drinks are limited to 300 ppm SS or 150 ppm BS; when mixed the maximum amounts are 250 ppm SS+150 ppm BS.

These preservatives are used for beverages and other fluid foodstuffs containing large amounts of water, generally in the form of their water-soluble sodium, calcium and potassium salts. The bactericidal effect, however, is developed exclusively by the undissociated acids. If the foodstuffs to be preserved with benzoic acid and/or sorbic acid contain ascorbic acid, then there exists the danger that, through a reaction of the ascorbic acid with the benzoic acid and/or the sorbic acid, undesired health hazardous reaction products could result.

The solubilities of the preservatives mentioned in water, ethanol and oil are:

| Substance | Water | 100% Ethanol | Plant Oil |
|---|---|---|---|
| Sorbic Acid | 0.16 g/100 g | 13 g/100 g | 1 g/100 g |
| Potassium Sorbate | 138 g/100 g | n.a. | n.a. |
| Benzoic Acid | 0.34 g/100 g | Very soluble | 2 g/100 g |
| Sodium Benzoate | 63 g/100 g | n.a. | n.a. |

The dissociation of the weak acid SS (pKs=4.8) and BS (pKs=4.22) is highly dependent on the pH-value of the medium, into which it is introduced. For pH-values, as is common for classic non-alcoholic drinks (pH=2.8-3.5), 90-100% of SS or BS is undissociated and thereby effective as bactericide. However, due to the poor water-solubility of the acids, a relatively high dose is necessary.

In products with low acidity, on the other hand, (pH-values 4.0—neutral), primarily for BS, considerable portions are dissociated that have no effect against microorganisms.

| pH Value | 3 | 3.5 | 4.0 | 5.0 |
|---|---|---|---|---|
| BS Anion, dis. | 6% | 16.7% | 38.7% | 86.5% |
| SS Anion, dis. | 1.7% | — | 14.7% | 63% |

The invention therefore has the task to better protect foodstuffs, primarily beverages, against the effects of microorganisms.

In addition, the invention provides a solubilisate of a preservative that is free of a stabilizing agent, which contains an aliphatic and/or aromatic acid such as sorbic acid and/or benzoic acid as well a one or more emulsifiers with a HLB value between 9 and 18. The concentration of emulsifier can lie between 50% and 95% with regards to the total amount of the solubilisate. The sorbic or benzoic acid or the mixture of the two can be contained in the solubilisate in an amount between 5% and 50%. It is advisable to use a polysorbate as the emulsifier, preferably polysorbate 20 and/or polysorbate 80.

Figure 1:
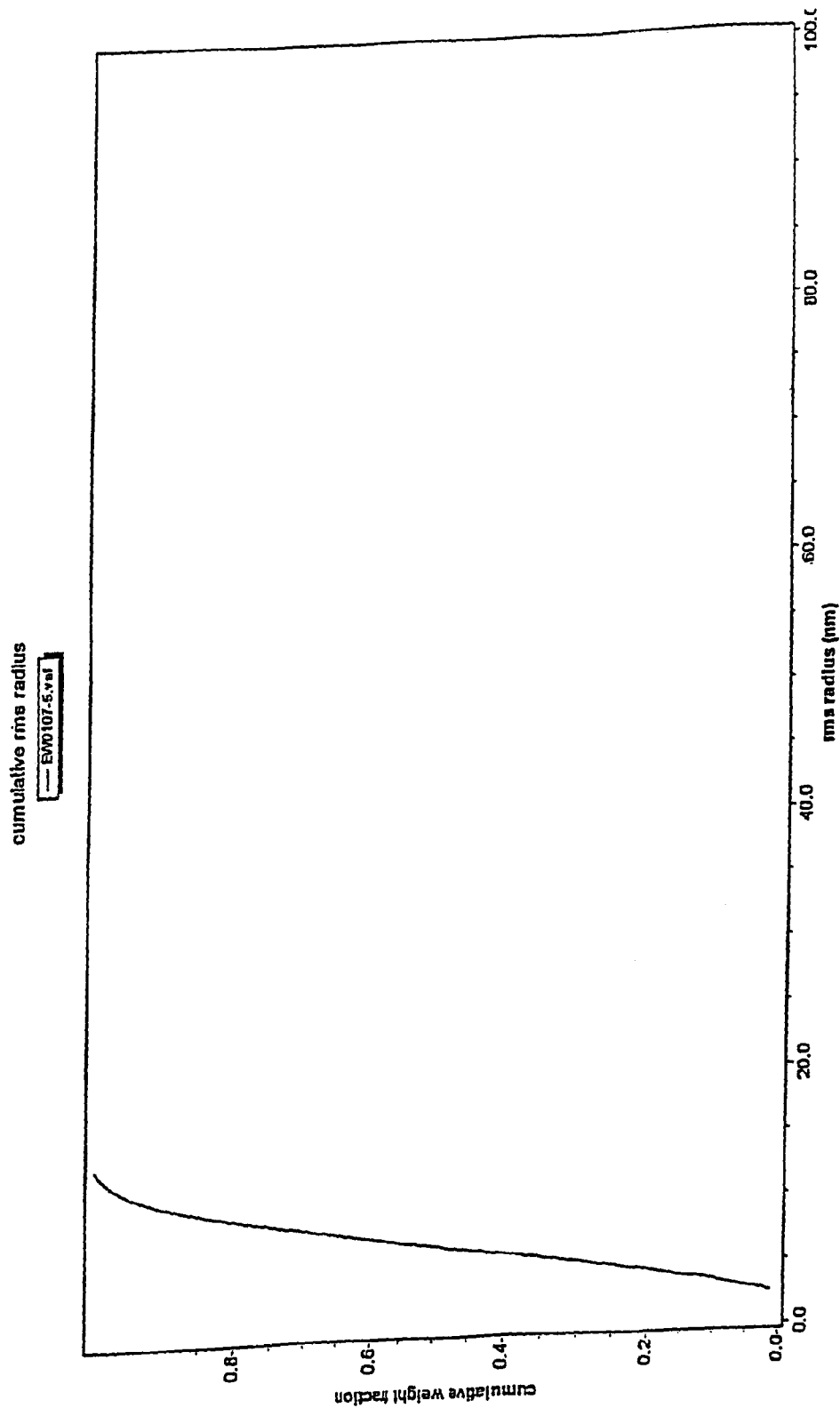
FIGS. 1 and 2 graphically represent the results of testing the present invention.

The solubilisate according to the invention has an excellent bactericidal effect. For example, if agar is given to a nutrient solution, on the one hand 500 mg potassium sorbate and on the other hand in comparison 500 mg sorbic acid-solubilisate with polysorbate 20, after about three weeks contact time with potassium sorbate there results a bacteria count of $1.6 \times 10^{10}$, compared to a bacteria count of $3.5 \times 10^8$ with a sorbic acid-solubilisate, in other words a bacteria count smaller by almost two orders of magnitude.

The invention is based on the concept of slowing or preventing a dissociation of the organic aids primarily in media that are only weakly acidic through micellation, with the consequence that more undissociated acid is available for the elimination of microorganisms. Therefore, the dose of the micellated organic acids can be lowered considerably. Since the micelles only open upon contact with cell membranes or similar biological material, the acid released from the micelles can work directly on the microorganisms to eliminate them.

The invention can be used for foodstuffs of all kinds, in particular in non-alcoholic beverages with high pH values from about 4.0 to 7.0, such as tea, coffee, cocoa and milk beverages. The preservative solubilisates are added to the relevant tea, coffee, cocoa and milk drinks. The dosing occurs individually by the producer of the end product between 100 ppm and 500 ppm, which means, assuming a twenty percent benzoic acid solubilisate between 500 ppm and 1000 ppm per liter of end product.

The invention can furthermore be used for the preservation of milk products such as milk, cheese and yogurt. The solubilisates are applied primarily to the cheese rind. The sorbic acid solubilisate may also be put in small amounts in cheese. Moreover, vegetables, fruits and herbs can be submerged in a water solution of the solubilisate according to the invention and thereby be better protected against mold, mildew and yeasts and also made longer-lasting. Finally, the invention also allows for the preservation of surfaces of wood or other artificial materials, so that, for example, furniture or the surfaces of medical apparatus and devices can be treated for preservation with solubilisates in diluted watery solution.

The bactericidal effect of a benzoic acid solubilisate, for example, arises from an investigation of a publically ordered and sworn expert for foodstuff chemistry.

Test materials:
1) Benzoic acid: raw material benzoic acid, company Merck Art. No. 1.00136
2) Benzoic acid solubilisate solution: raw material 20% solution of benzoic acid solubilisate, company AQUA-NOVA Lot-No. L096.06.LM.01.01
3) Nutrient solution: Yeast Malt Broth, company Sigma Art. No. Y 3752
4) Nutrient Agar: see 3) with addition of agar, company Fluka Art. No. 05040, 20 g per liter nutrient solution
5) Yeast culture: *Saccharomyces cerevisae*, company DSMZ Art. No. 7044

The composition of the 20% solution of benzoic acid solubilisate according to 2) is given in the following examples under EW0108/8.

The following table 1 shows the influence of benzoic acid on the yeast growth and table 2 gives the inhibition of the yeast growth achieved, each at pH 6.2 and room temperature. Table 1 shows that even with a benzoic acid concentration of tains about 20% benzoic acid and about 80% polysorbate 20 is advisable. Furthermore, it is advisable for many applications, for example for an addition to acidified beverages, if the benzoic acid solubilisate contains a portion of the surfactant, which binds the micellated benzoic acid, that free benzoic acid is practically non-existent in the beverage. If the beverage is, for instance, offset with ascorbic acid, then the effect of the ascorbic acid on the benzoic acid can easily cause the formation of damaging benzol. The benzoic acid solubilisate according to the present invention prevents the formation of benzol in acidified beverages. The surfactant advisably includes a mixture of an oil containing primarily middle-chain triglyceride with a small portion of wax, Cera alba, for example.

The surfactant can be represented in the benzoic acid solubilisate with a concentration of about 2% to 10%, whereby about 3% to 10% could fall upon the oil and about 1% to about 2% could fall upon the wax.

In detail, a benzoic solubilisate proves to be especially favorable in its bactericidal effect, when it contains about 21% benzoic acid, about 5% of a primarily middle-chain triglyceride oil, about 73% polysorbate 20 and about 1% of a wax, such as beeswax (Cera alba). Instead of polysorbate 20, polysorbate 80 can be used in about the same amount in the benzoic acid solubilisate. Finally, another embodiment comprises a solubilisate of about 5% sorbic acid, about 5% benzoic acid about 90% polysorbate 20.

Benzoic Acid (Weighted Sample Benzoic Acid+50 ml Nutrient Solution (pH 6.2)+50 ml Water+0.4 ml Yeast Solution)

| Benzoic Acid Concentration | 10 ppm | 50 ppm | 100 ppm | 200 ppm | 300 ppm | 500 ppm |
|---|---|---|---|---|---|---|
| Initial Bacteria Count | 2,900/ml | 2,900/ml | 2,900/ml | 2,900/ml | 2,900/ml | 2,900/ml |
| After 3 days | 1,650,000/ml | 1,900,000/ml | 670,000/ml | 510,000/ml | 630,000/ml | 700/ml |
| After 7 days | 1,200,000/ml | 1,100,000/ml | 530,000/ml | 430,000/ml | 400,000/ml | 55,000/ml |
| After 15 days | 800,000/ml | 900,000/ml | 600,000/ml | 350,000/ml | 520,000/ml | 230,000/ml |
| After 22 days | 1,100,000/ml | 930,000/ml | 1,200,000/ml | 400,000/ml | 250,000/ml | 120,000/ml |
| After 29 days | 1,300,000/ml | 1,300,000/ml | 900,000/ml | 400,000/ml | 230,000/ml | 43,000/ml |

500 ppm, there is still a high yeast growth after 29 days of contact time. In comparison, Table 2 shows that with a benzoic acid concentration of 500 ppm in solubilisate, the yeast 2.) Benzoic Acid Solubilisate (Weighted Sample Solubilisate+50 ml Nutrient (pH 6.2)+50 ml Water+0.1 ml Yeast Solution)

| | Solubilisate Addition | | | | | |
|---|---|---|---|---|---|---|
| | 50 ppm | 250 ppm | 500 ppm | 1000 ppm | 1500 ppm | 2500 ppm |
| | Benzoic Acid Concentration | | | | | |
| | 10 ppm | 50 ppm | 100 ppm | 200 ppm | 300 ppm | 500 ppm |
| Initial Bacteria Count | 5,500/ml | 5,500/ml | 5,500/ml | 5,500/ml | 5,500/ml | 5,500/ml |
| After 3 days Apr. 28, 2006 | 1,990,000/ml | 4,170,000/ml | 800,000/ml | 235,000/ml | 229,000/ml | 1,520/ml |
| After 9 days May 4, 2006 | 790,000/ml | 3,100,000/ml | 630,000/ml | 360,000/ml | 185,000/ml | 500/ml |
| After 15 days May 10, 2006 | 2,250,000/ml | 815,000/ml | 85,000/ml | 65,000/ml | 37,000/ml | 15/ml |
| After 22 days May 17, 2006 | 4,325,000/ml | 750,000/ml | 50,000/ml | 35,000/ml | 12,000/ml | n.n. in 1 ml | growth is considerably slowed after beginning the addition of the solubilisate and that after 29 days of contact time the yeast is completely eliminated. Even after the third day of contact, a benzoic acid concentration in solubilisate of 300 ppm leads to a continuous growth reduction of the yeast.

Preferred embodiments of the solubilisate invention are given in the subclaims. It is recommended when the sorbic acid solubilisate exhibits about 5% sorbic acid and 95% polysorbate 20. For the benzoic acid, a solubilisate that con- Subsequently, without limiting the generality of the patent claims, five preferred methods of formulation will be shared, which also contain information about the corresponding method of production of the individual solubilisates. In the simplest form of the manufacturing process, this is designed so that the emulsifier is warmed to about 7° C. up to about 90° C., in the case of the polysorbate 20 to about 72° C. up to about 85° C., preferably warmed to about 80° C. up to about 85° C., the aliphatic and/or the aromatic acid is slowly, that means without considerable (max. 5° C.) cooling of the emulsifier, while being stirred, worked into the warm emulsifier, after complete mixing, the mixture is further warmed to about 83° C. up to about 90° C., while being constantly stirred, and is well homogenized. Then the solubilisate is allowed to cool for bottling to under 35° C., whereby it is recommended that the mixture be cooled quickly to 40° C. It is advisable to introduce an emulsifier of about 50% to about 95%, such as polysorbate 20 and/or polysorbate 80, into the production procedure. For the aliphatic and/or aromatic acid it is recommended that about 5% to about 50% be used.

If the benzoic acid solubilisate contains a surfactant, one should proceed, so that first the surfactant is warmed to about 55° C. up to about 65° C., preferably 58° C. up to about 62° C., and homogenized, that the benzoic acid is added to the warm surfactant and homogenized again while being stirred, that then about one fifth of the polysorbate amount, so about 150 g per kg solubilisate, is added to the benzoic acid/surfactant mixture and the mass thereby obtained is warmed while being stirred to about 80° C. up to about 90° C. and homogenized and that then, the rest of the polysorbate, so four fifths of it, is added slowly, stirred and the temperature held at about 80° C. to 90° C. for at least 5 minutes. Then if necessary, it can be cooled quickly to 40° C. and bottled at about 35° C. In this procedure about 2% to about 10% surfactant can be used. If in the preferred design of the procedure, a mixture of an oil containing predominantly middle-chain triglyceride and a wax is used, it is advisable to work in about 1% to 1.5% of the wax into about 5% of the oil warmed as described and to homogenize the mixture and finally add about 20% benzoic acid and then add, as described above, the polysorbate. Otherwise, the preferred methods for the procedure according to the present invention are given in the procedure claims.

Figure 2:
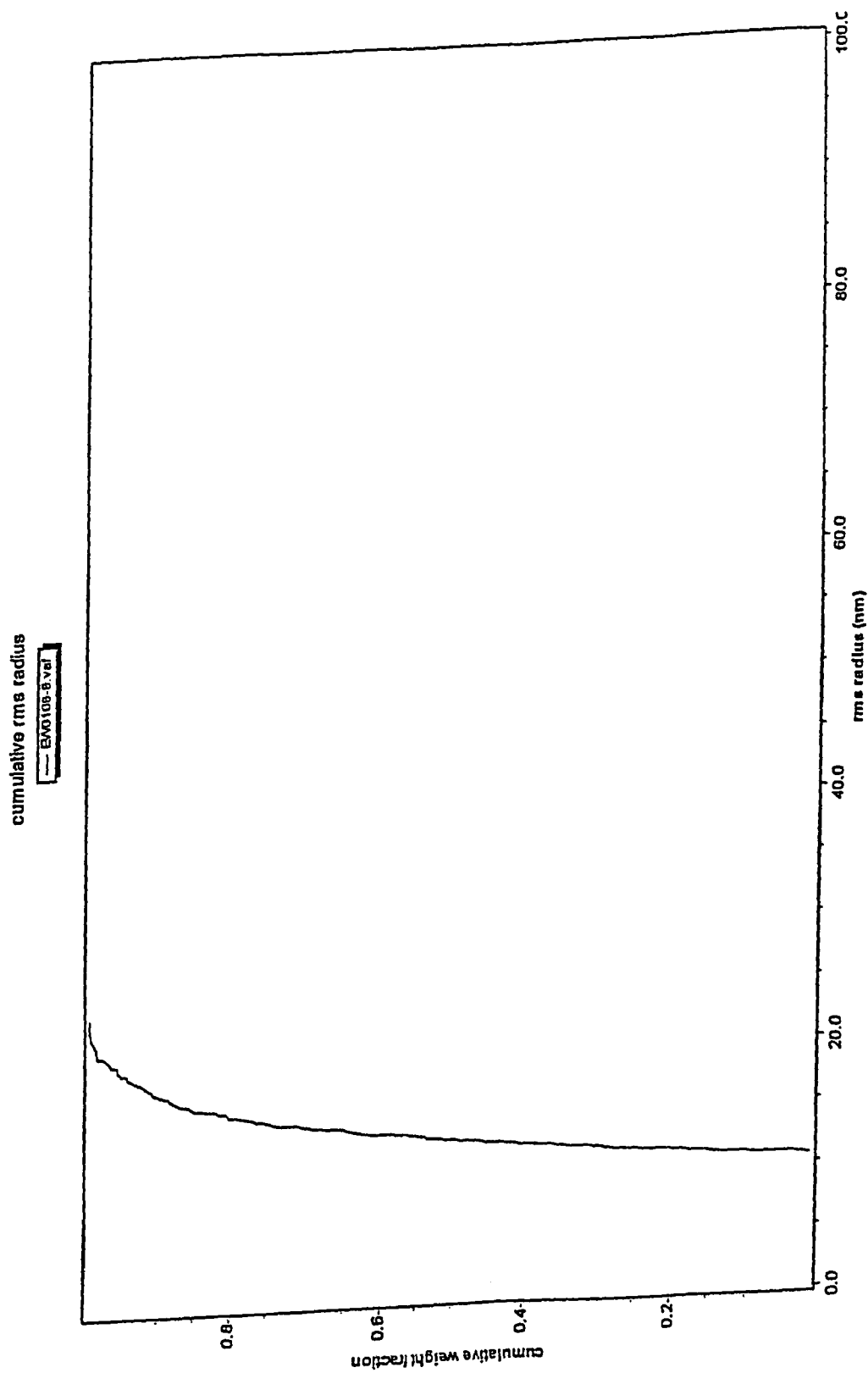

For the solubilisate according to the present invention, the radius distributions of the micelles formed have been measured. The result is shown in the attached FIGS. 1 and 2. The measurements were conducted according to the field-flow method of the Wyatt Technologie Europe GmbH. FIG. 1 refers to the 5% sorbic acid solubilisate and FIG. 2 applies for the 20% benzoic acid solubilisate. Recognizable is that the middle micelle radius for the sorbic acid solubilisate lies under 10 nm and the middle micelle radius for the benzoic acid solubilisate lies under 20 nm.

In the formulations MCT means medium chain triglyceride. The weight information in percent refer to the total weight of the solubilisate=100%.

| EW-No.: | EW0108/8 |
| --- | --- |
| Label: | Water and Fat Soluble |
|  | 20% Benzole Acid Solubilisate |

Ingredients:

| 200 g | Benzoic acid; AppliChem |
| --- | --- |
|  | (AGT-Material No.: 10080/079) |
| 800 g | Polysorbate 20; Lamesorb SML 20; |
|  | Cognis AGT-Material No.: 10520/016) |

Procedure:
Heat polysorbate 20 to 80-85° C.
Stir in benzoic acid slowly.
Stir continuously, heat to max. 90° C. and homogenize well.
Allow to cool to <35° C. and bottle.

Appearance:
Light yellow, viscous, transparent
Storage Conditions:

| Dark, at room temperature (<25° C.) | |
| --- | --- |
| [watermark:] EW | |
| EW-No.: | EW0108/80/CA |
| Label: | NovaSol ® Benzoic |
|  | Water and fat soluble |
|  | 20% Benzoic Acid Solubilisate |

Ingredients:

| 210 g | Benzoic acid, AppliChem |
| --- | --- |
|  | (AGT-Material No.: 10080/079) |
| 50 g | Delios VK kosher (MCT-oil); Cognis |
|  | (AGT-Material No.: 10460/016) |
| 739 g | Polysorbate 80; Lamesorb SMO 20; Cognis |
|  | (AGT-Material No.: 10530/016) |
| 1 g | Cera alba (beeswax); Roeper |
|  | (AGT-Material No.: 10741/075) |

Procedure:
Warm MCT-oil (58-62° C.) and Cera alba slowly; stir to mix homogenously.
To the mixture, add benzoic acid and homogenize well by stirring (58-62° C.)
Add about 20% of the polysorbate 80 quantity (approx. 150 g/kg) and stir while heating to 83-87° C. until the mixture is homogenous.
Slowly add the rest of the polysorbate 80 quantity, stir well and hold the temperature at 83-87° C. for at least 5 minutes.
Stir constantly while lowering the temperature as quickly as possible to 40° C.
Bottle at 40° C. or cooler.
Appearance:
Light yellow/white, viscous
Storage Conditions:

| Dark, at room temperature (<25° C.) | |
| --- | --- |
| [watermark:] EW | |
| EW-No.: | EW0109/12 |
| Label: | Water and Fat Soluble |
|  | 5% Sorbic Acid/ |
|  | 5% Benzole Acid Solubilisate |
|  | (Combination) |

Ingredients:

| 50 g | Sorbic acid; Krämer & Martin |
| --- | --- |
|  | (AGT-Material No.: 10642/88) |
| 50 g | Benzoic acid; AppliChem |
|  | (AGT-Material No.: 10080/079) |
| 900 g | Polysorbate 20; Lamesorb SML 20; |
|  | Cognis (AGT-Material No.: 10520/016) |

Procedure:
Mix sorbic and benzoic acid.
Warm polysorbate 20 to 80-85° C.
Stir powder mixture into polysorbate (83-87%).
Heat everything, while stirring, to about 88-92° C. and homogenize well.
Cool to <35° C. and bottle.

Appearance:
  Yellow, viscous, transparent
Storage Conditions:

| Dark, at room temperature (<25° C.) |
| [watermark:] EW |
| EW-No.: | EW0108/CA/1 |
| Label: | NovaSOL ® Benzoic Water and fat soluble 20% Benzoic Acid Solubilisate |

Ingredients:

| 210 g | Benzoic acid, AppliChem (AGT-Material No.: 10080/079) |
| 50 g | Delios VK kosher (MCT-oil); Cognis (AGT-Material No.: 10460/016) |
| 738.5 g | Polysorbate 20; Lamesorb SML 20; Cognis (AGT-Material No.: 10520/016) |
| 1.5 g | Cera alba (beeswax); Roeper (AGT-Material No.: 10741/075) |

Procedure:
Warm MCT-oil (58-61° C.) and Cera alba slowly; stir to mix homogenously.
To the mixture, add benzoic acid and homogenize well by stirring (58-62° C.).
Add about 20% of the polysorbate 20 quantity (approx. 150 g/kg) and stir while heating to 83-87° C. until the mixture is homogenous.
Slowly add the rest of the polysorbate 20 quantity, stir well and hold the temperature at 83-87° C. for at least 5 minutes.
Stir constantly while lowering the temperature as quickly as possible to 40° C.
Bottle at 40° C. or cooler.
Appearance:
  Light yellow/white, viscous
Storage Conditions:

| Dark, at room temperature (<25° C.) |
| EW-No.: | EW0107/5 |
| Label: | Water and Fat Soluble 5% Sorbic Acid Solubilisate |

Ingredients:

| 50 g | Sorbic acid; AppliChem (AGT-Material No.: 10641/079) |
| 950 g | Polysorbate 20; Lamesorb SML 20; Cognis AGT-Material No.: 10520/016) |

Procedure:
Heat polysorbate 20 to 72-77° C.
Stir in sorbic acid slowly.
Stir continuously, heat to max. 90° C. and homogenize well.
Allow to cool to <35° C. and bottle.
Appearance:
  Light yellow, viscous, transparent
Storage Conditions:
  Dark, at room temperature (<25° C.)

The invention claimed is:

1. A water-free solubilisate of a preservative containing benzoic acid that, but for the presence of one or more emulsifiers with an HLB value between 9 and 18, is free of stabilizing agents, with a concentration of about 50% and about 95% emulsifier (w/w) with regard to the total quantity of the solubilisate, wherein the acid is in protonated form, the solubilisate further comprising a surfactant comprising an oil containing predominantly medium chain triglycerides and a wax,
  wherein the emulsifier is a polysorbate and the surfactant is present in the solubilisate with a concentration of about 2 to 10 wt. %, whereby about 3 to 10 wt. % fall upon the oil and about 1 to about 2 wt. % fall upon the wax.

2. The solubilisate according to claim 1, wherein the concentration of the benzoic acid is between 5% and 50% (w/w).

3. The solubilisate according to claim 1, consisting of about 20% benzoic acid (w/w), about 5% of an oil containing predominately medium chain triglycerides (w/w), about 73.5% polysorbate 20 (w/w) and about 1.5% of a wax (w/w).

4. The solubilisate according to claim 3, wherein the wax is beeswax in the form of Cera alba.

5. The solubilisate according to claim 1, consisting of about 20% benzoic acid (w/w), about 5% of an oil containing predominately medium chain triglycerides (w/w), about 73.5% polysorbate 80 (w/w) and about 1.5% of a wax (w/w).

6. A method for producing a solubilisate according to claim 1, in which benzoic acid is added to a heated and homogenized surfactant, said surfactant comprising a mixture of an oil containing predominantly medium-claim triglycerides and a wax, wherein the surfactant is present in the solubilisate with a concentration of about 2 to 10 wt % and wherein about 3 to 10 wt.-% fall upon the oil and about 1 to about 2 wt. % fall upon the wax, and the benzoic acid/surfactant mixture is homogenized, that after about a fifth of the polysorbate quantity is added to the benzoic acid/surfactant mixture and the resultant mass is stirred and heated and homogenized and finally the rest of the polysorbate quantity is slowly added and stirred at about 80° C. to about 90° C.

7. The method according to claim 6, in which the surfactant is heated to about 55° C. to about 65° C.

8. The method according to claim 6, in which the surfactant is mixed from about 5% of the oil and about 1% to about 1.5% of the wax.

9. A foodstuff comprising the water-free solubilisate according to claim 1.

10. The foodstuff according to claim 9, wherein the foodstuff is a non-alcoholic beverage with a high pH value from about 4.0 to about 7.0, and wherein the solubilisate is present in the non-alcoholic beverage in an amount between 500 ppm and 1000 ppm per liter.

11. A foodstuff according to claim 9, wherein the foodstuff is selected from the group consisting of milk products, milk, cheese and yogurt.

12. A foodstuff according to claim 9, wherein the foodstuff is selected from the group consisting of vegetables, fruits and herbs.

13. A process for the treatment of an object comprising applying a watery solution comprising the solubilisate according to claim 1 and water to the object.

* * * * *